US00PP26422P2

(12) United States Plant Patent
Jamieson

(10) Patent No.: US PP26,422 P2
(45) Date of Patent: Feb. 16, 2016

(54) *AGAPANTHUS* PLANT NAMED 'BLUE FLARE'

(50) Latin Name: *Agapanthus praecox*
Varietal Denomination: Blue Flare

(71) Applicant: Richard Jamieson, Kirstenhof (ZA)

(72) Inventor: Richard Jamieson, Kirstenhof (ZA)

(73) Assignee: THE PINK GERANIUM NURSERY, Elsenburg (ZA)

( * ) Notice: Subject to any disclaimer, the term of this patent is extended or adjusted under 35 U.S.C. 154(b) by 10 days.

(21) Appl. No.: 13/999,107

(22) Filed: Jan. 13, 2014

(51) Int. Cl.
*A01H 5/02* (2006.01)

(52) U.S. Cl.
USPC ..... Plt./398

(58) Field of Classification Search
USPC ..... Plt./398
CPC ..... A01H 5/02
See application file for complete search history.

(56) References Cited

PUBLICATIONS http://www.blackdogplants.co.za/gallery.htm 1 page, 2010.*

* cited by examiner

*Primary Examiner* — Kent L Bell
(74) *Attorney, Agent, or Firm* — Penny J. Aguirre

(57) ABSTRACT

A new cultivar of *Agapanthus* named 'Blue Flare', characterized by its mid season blooming habit and re-blooms for up to 6 weeks, its blue self-cleaning flowers that are held primarily upright from pedicels (not drooping), and its medium tall plant height.

2 Drawing Sheets

Botanical classification: *Agapanthus praecox*.
Varietal denomination: 'Blue Flare'.

BACKGROUND OF THE INVENTION

The present invention relates to a new and distinct cultivar of *Agapanthus praecox* and will be referred to hereafter by its cultivar name, 'Blue Flare'. 'Blue Flare' represents a new perennial herb grown for landscape use.

The new *Agapanthus* originated as the result of an on going breeding program in Cape Town, Republic of South Africa. The goal of the breeding program was to produce a cultivar of *Agapanthus* of medium size with a re-blooming habit.

'Blue Flare' originated as a seedling that arose from seed planted from open pollination of an unnamed plant of *Agapanthus praecox* from the Inventor's breeding program in 2002. The male parent is unknown. The new *Agapanthus* was selected as a single unique plant in December of 2004.

Asexual propagation of the new cultivar was first accomplished by in vitro propagation under the direction of the Inventor in December of 2005 in Cape Town, Republic of South Africa. Asexual propagation by division and tissue culture has determined that the characteristics of this cultivar are stable and are reproduced true to type in successive generations.

SUMMARY OF THE INVENTION

The following traits have been repeatedly observed and represent the characteristics of the new cultivar. The characteristics in combination distinguish 'Blue Flare' as a distinct cultivar of *Agapanthus*.

1. 'Blue Flare' exhibits a mid season blooming habit and re-blooms for up to 6 weeks.

2. 'Blue Flare' exhibits blue flowers that are held primarily upright from pedicels (not drooping.
3. 'Blue Flare' exhibits flowers that are self-cleaning.
4. 'Blue Flare' exhibits a medium-tall plant height.

The female parent differs from 'Blue Flare' in having flowers that are drooping, not re-blooming and not self-cleaning. 'Blue Flare' can be compared to the cultivars 'Peter Pan' (not patented) and 'Snowball' (not patented). 'Peter Pan' is similar to 'Blue Flare' in being evergreen and in having blue flowers, but 'Peter Pan' differs from 'Blue Flare' in being shorter in plant height, in having flowers that are held more outward, and in lacking a re-blooming habit. 'Snowball' is similar to 'Blue Flare' in being evergreen, in having full flower heads and a re-blooming habit. 'Snowball' differs from 'Blue Flare' in having white flowers and a shorter plant height.

BRIEF DESCRIPTION OF THE DRAWINGS

The accompanying colored photographs illustrate the overall appearance and distinct characteristics of the new *Agapanthus*. The photographs were taken of a four year-old plant of 'Blue Flare' as field grown outdoors in Cape Town, Republic of South Africa.

The photograph in FIG. 1 provides a close-up view of an inflorescence of 'Blue Flare'.

Figure 1:
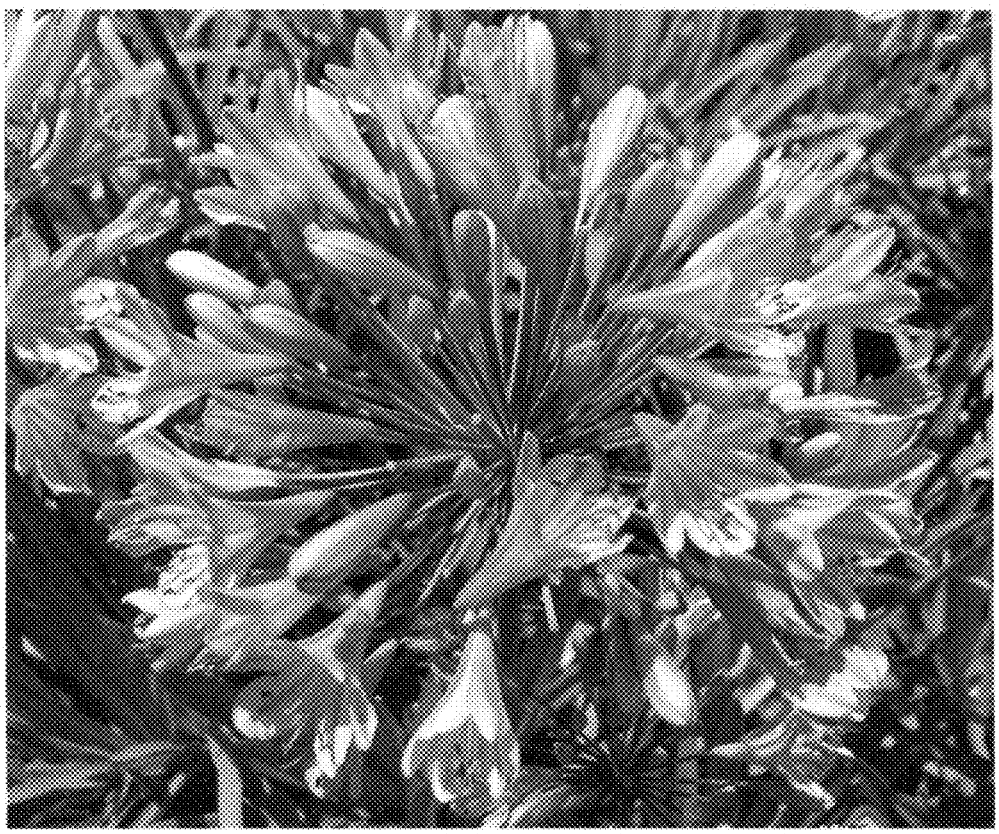
Figure 2:
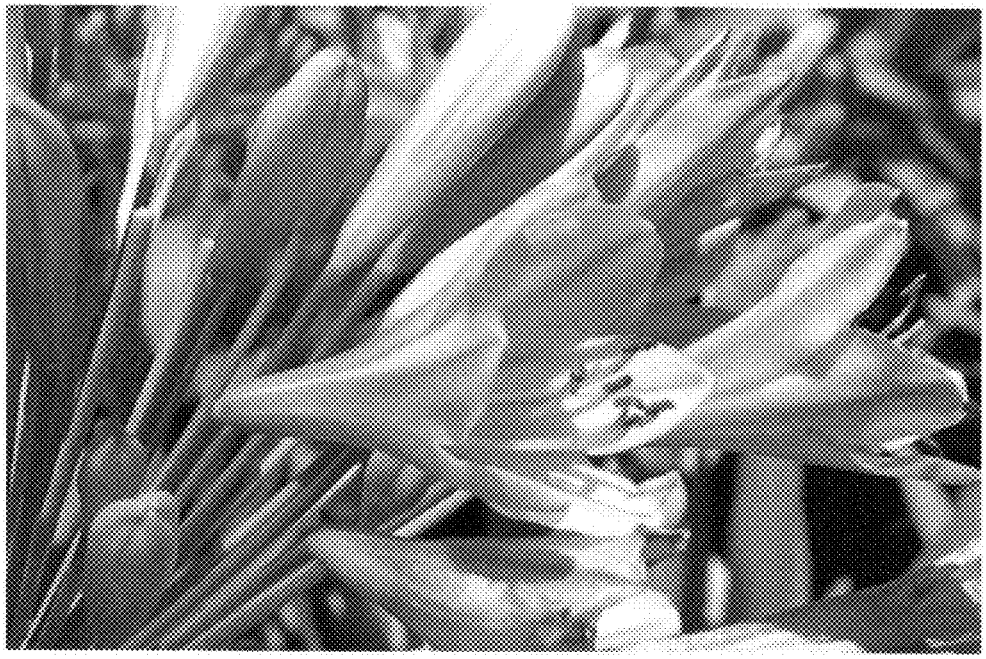

The photograph in FIG. 2 provides a close-up view of the flowers of 'Blue Flare'.

The colors in the photographs are as close as possible with the photographic and printing technology utilized and color values cited in the detailed botanical description accurately describe the colors of the new *Agapanthus*.

DETAILED BOTANICAL DESCRIPTION

The general observations and descriptions describe plants about four year-old in age as grown outdoors under field conditions in Cape Town, Republic of South Africa. The phenotype of the new cultivar may vary with variations in environmental, climatic, and cultural conditions, as it has not been tested under all possible environmental conditions. The color determinations are in accordance with The 2007 R.H.S. Colour Chart of The Royal Horticultural Society, London, England, except where general color terms of ordinary dictionary significance are used.

General description:

*Blooming period.*—Re-blooms for up to 6 weeks in mid summer in Cape Town, Republic of South Africa.

*Plant type.*—Evergreen perennial herb.

*Plant habit.*—Upright with cascading foliage.

*Height and spread.*—Reaches a height of about 80 cm in bloom and a spread of about 50 cm.

*Cold hardiness.*—At least to U.S.D.A. Zone 8.

*Diseases and pests.*—No susceptibility or resistance to diseases or pests has been observed.

*Root description.*—Fleshy main roots and fibrous secondary roots.

*Propagation.*—Tissue culture and division.

*Root development.*—A division will root and finish in a 6-inch container in about 90 days at 25° C. with high light intensity.

*Growth rate.*—Moderate.

Foliage description:

*Leaf shape.*—Linear.

*Leaf division.*—Simple.

*Leaf base.*—Cuneate.

*Leaf arrangement.*—2-ranked, in rosette.

*Leaf apex.*—Acute.

*Leaf aspect.*—Emerging leaves erect, then cascade.

*Leaf venation.*—Parallel, color matches leaf coloration.

*Leaf margins.*—Entire.

*Leaf size.*—Average of 53 cm in length and 2.8 cm in width.

*Leaf surface.*—Glabrous, slightly glossy.

*Leaf substance.*—Thick and leathery, moderate to high durability to stress.

*Leaf number.*—Average of 20 per rosette.

*Leaf color.*—Young leaves, upper surface; Yellow-Green 144A young leaves, lower surface; Yellow Green 146B mature leaves, upper surface; Yellow-Green 144A and White 157B near base, mature leaves, lower surface; Yellow-Green 146C and White 157B near base.

*Leaf attachment.*—Sessile to crown.

Flower description:

*Inflorescence type.*—Simple umbel.

*Flower fragrance.*—None.

*Flower type.*—Campanulate.

*Flower number.*—Full flower heads; an average of about 60 flowers per umbel, one umbel per peduncle and one peduncle per rosette.

*Inflorescence size.*—Average of 9 cm in depth and 15 cm in diameter.

*Flower size.*—About 3.7 cm in depth and 1.2 cm in width.

*Lastingness of inflorescence.*—About 35 days.

*Longevity as a cut flower.*—About 1 week.

*Flower aspect.*—Held primarily upright from pedicel.

*Peduncle.*—Strong, somewhat flattened, held erect, average of 90 cm in length and 1.2 cm in width at distal region and 10 mm in width at proximal region, surface is glabrous, color Yellow-Green 144B.

*Pedicels.*—Strong, average of 5 cm in length and 2 mm in width, held erect to outward, color Yellow-Green 144A, surface is glabrous.

*Flower buds.*—Obovate in shape, average of 3 cm in length and 11 mm in width, color Violet Blue 92B.

*Tepals.*—6, narrow obovate in shape, entire margin, glabrous texture, acute apex, average of 3 cm in length and 10 mm in width, color when young inner surface; Violet-Blue 91C, color when young outer surface; Violet-Blue 91B, color mature inner surface; Violet-Blue 91D, color mature outer surface; Violet-Blue 91C, mid rib on all surfaces Violet-Blue 92A.

Reproductive organs:

*Gynoecium.*—1 pistil, average of 2 cm in length, stigma is narrow clavate in shape and Violet-Blue 91B in color, style is about 2.5 cm in length and Violet-Blue 97B in color, ovary is Yellow-Green 150B in color.

*Androecium.*—6 stamens, anthers are dorsified, oblong in shape, average of 2 mm in length, and Violet Blue 91B in color, filament is 2 cm in length, pollen is low in quantity and Brown 199B in color.

*Fruit/seed.*—Have not been observed.

It is claimed:

1. A new and distinct cultivar of *Agapanthus* plant named 'Blue Flare' as herein illustrated and described.

* * * * *